United States Patent [19]

McGeehan et al.

[11] Patent Number: 5,234,813
[45] Date of Patent: Aug. 10, 1993

[54] METHOD AND DEVICE FOR METERING OF FLUID SAMPLES AND DETECTION OF ANALYTES THEREIN

[75] Inventors: John K. McGeehan, Woodbury; Gerhard Ertingshausen, Princeton, both of N.J.

[73] Assignee: Actimed Laboratories, Inc., Mount Laurel, N.J.

[21] Appl. No.: 749,521

[22] Filed: Aug. 26, 1991

Related U.S. Application Data

[63] Continuation-in-part of Ser. No. 352,985, May 17, 1989, Pat. No. 5,087,556.

[51] Int. Cl.[5] .................. G01N 33/543; G01N 33/544
[52] U.S. Cl. .......................... 435/7.9; 422/55; 422/56; 422/57; 422/58; 435/7.92; 435/970; 436/164; 436/169; 436/518; 436/807; 436/808; 436/809; 436/805; 436/810
[58] Field of Search .............. 435/7.9, 7.92, 970; 436/164, 169, 518, 805, 807–810; 422/56–58, 61, 55, 101

[56] References Cited

U.S. PATENT DOCUMENTS

| | | | |
|---|---|---|---|
| 3,540,857 | 11/1970 | Martin | 23/292 |
| 3,915,647 | 10/1975 | Wright | 436/805 |
| 3,964,871 | 6/1976 | Hochstrasser | 422/58 |
| 4,042,329 | 8/1977 | Hochstrasser | 422/58 |
| 4,435,504 | 3/1984 | Zuk et al. | 422/56 |
| 4,477,575 | 10/1984 | Vogel et al. | 436/170 |
| 4,594,327 | 6/1986 | Zuk | 436/514 |
| 4,605,629 | 8/1986 | Lange et al. | 422/58 |
| 4,738,823 | 4/1988 | Engelmann | 422/58 |
| 4,756,884 | 7/1988 | Hillman et al. | 422/73 |
| 4,761,381 | 8/1988 | Blatt et al. | 422/58 |
| 4,810,470 | 3/1989 | Burkhardt et al. | 422/56 |
| 4,906,439 | 3/1990 | Grenner | 422/58 |
| 4,959,324 | 9/1990 | Ramel et al. | 436/169 |
| 4,960,691 | 10/1990 | Gordon et al. | 436/810 |
| 4,987,085 | 1/1991 | Allen et al. | 422/56 |
| 4,999,287 | 3/1991 | Allen et al. | 422/56 |
| 5,006,309 | 4/1991 | Khalil et al. | 422/58 |

FOREIGN PATENT DOCUMENTS

| | | |
|---|---|---|
| 0014797 | 9/1980 | European Pat. Off. |
| 0408223 | 1/1991 | European Pat. Off. |
| 0430248 | 6/1991 | European Pat. Off. |
| 9011519 | 10/1990 | World Int. Prop. O. |
| 9014161 | 11/1990 | World Int. Prop. O. |
| 9101179 | 2/1991 | World Int. Prop. O. |
| 9102589 | 3/1991 | World Int. Prop. O. |

OTHER PUBLICATIONS

Clin. Chem. 30: (10) 1705–1707 (1984).

*Primary Examiner*—David Saunders
*Assistant Examiner*—Christopher L. Chin
*Attorney, Agent, or Firm*—Iver P. Cooper

[57] ABSTRACT

An analytical device for fluid samples includes a fluid sample well means connected to a sample initiation area in such a fashion that the assay will not commence unless sufficient sample is introduced into the sample well means to conduct the assay. Once sufficient sample has been deposited into the sample well means, the sample flows into an initiation area and the assay commences.

17 Claims, 5 Drawing Sheets

METHOD AND DEVICE FOR METERING OF FLUID SAMPLES AND DETECTION OF ANALYTES THEREIN

The present application is a continuation-in-part of Ser. No. 07/352,985, filed May 17, 1989, now U.S. Pat. No. 5,087,556 which application is hereby incorporated in its entirety by reference.

FIELD OF THE INVENTION

The present invention relates to a method and device for metering a fluid sample prior to introducing the fluid sample into an assaying device for quantitative or qualitative measurement of an analyte, such as a dipstick, analytical slide, or the like.

BACKGROUND OF THE INVENTION

A number of non-instrumented devices have heretofore been developed for measuring analytes in fluid samples, such as dipsticks, reagent-impregnated slides, and the like. However, although these devices have the advantage of being inexpensive and easy to use, they have the disadvantage of not providing a means for determining if sufficient sample has been introduced to the device to provide an accurate measurement of the analyte. For example, if an insufficient amount of sample is introduced to the device, a false low reading may be obtained.

Medical science in particular has an increasing need for quick, accurate determination of analytes in blood or other body fluids. Traditionally, assays for analytes have been performed by laboratories and have required skilled technicians, complex apparatus and reagents, and considerable time in order to determine accurate results. Numerous qualitative and some quantitative devices and methods have been developed which allow the lay person to perform self-testing at home or outside of a traditional laboratory. Many of these devices and methods include test strips or dip sticks which can be exposed to blood or other body fluids in order to identify or quantify a component of body fluid. A common example of this technology includes the various test products for determining the concentration of blood glucose in diabetics.

The determination of the concentration of glucose and other analytes has heretofore been performed by various devices and methods using either urine or blood as the body fluid sample. The most common of these test are dip sticks from testing the concentration of glucose in urine. The dip sticks are dipped into a sample of urine and then undergo a color change. The color of the dip stick is compared to a chart of color references on the label of the container providing the dip stick. When the color of the dip stick is matched to the color reference, one determines the approximate glucose concentration from the color reference. Similar tests exist wherein paper strips are used to determine the concentration of glucose in whole blood. These tests are also conducted by comparing the amount of color formation of the paper strip to a standard. These semi-quantitative tests do not accurately determine the concentration of an analyte in the blood being tested unless an instrument is also used.

Devices have been proposed which detect and quantitatively measure analytes in body fluids, such as whole blood. When a drop of blood or other body fluid, such as urine, is applied to the device, the sample is drawn into consecutive compartments which separate solids from the liquid. In the case of whole blood, red blood cells are separated from the plasma. The filtered sample is then contacted with an enzymatic reagent to produce hydrogen peroxide. The hydrogen peroxide is reacted with a dye in a linear measurement zone, and the sample is drawn into a zone which serves to meter the quantity of sample which enters the measurement zone.

Although this type of device requires merely one or two drops of sample (about 40 to 80 $\mu$liters), if a sufficient amount of sample is not applied to the device a falsely low reading will be obtained. If, for example, the user does not wait for a full hanging drop to form from a finger stick, and wipes only a small quantity of blood on the entry to the device, less than 40 $\mu$liters of sample may be applied to the test device. If a sample of less than 40 $\mu$liters is applied to the device, this amount may conceivably be enough to initiate the reaction and cause a color change in the measurement zone, but not enough to fill the zone to full capacity, thereby giving a falsely low reading. One possible precaution against taking a false reading because of insufficient sample would be to have an end-of-test indicator in the draw zone, which only changes color when the draw zone is filled to capacity. However, an end-of-test indicator only signals that it is all right to read the results because a sufficient amount of sample has been drawn into the device to complete the test. If an insufficient amount of sample has been added, the test is ruined, because the chemical reactions in the device would have been initiated, but there would not be sufficient sample to provide an accurate result. Worse still, the user could ignore the absence of the end-of-test indicator and read the test result, which would be falsely low due to insufficient sample. Another problem with adding insufficient sample could be if the user adds more blood several minutes after addition of the first blood drop in an effort to complete the test. This could also give erroneous results due to discontinuous flow of the sample through the measurement zone (which could cause flow problems and time interval dependent changes in chemical reactions). Clearly, the optimal situation would be to delay the start of the test until a minimum amount of blood required to begin and complete the test has been transferred to the device.

Another problem connected with strip assay devices is that, as the fluid flows through the detection zone, the fluid flow is not even. Because the fluid flows more rapidly in the center of the zone, a "rocket-shaped" colored zone is formed. It may not be possible to determine the true end of the colored column.

Wright, in U.S. Pat. No. 3,915,647, discloses a device for determining the concentration of a substance in a fluid comprising a fluid receiving cavity of predetermined volume with an egress of relatively small dimensions. The fluid is disposed in the cavity and the proper amount is present when the cavity is totally filled or filled to a mark. The reagents which provide the colorimetric determination are preferably disposed in the cavity prior to the addition of the fluid. However, there is no provision for delaying the start of the reaction until sufficient fluid is added to the cavity.

Allen et al., in U.S. Pat. No. 4,987,085, disclose a filtering metering device in which various metering systems may be used to insure the substantial reproducibility of the amount of fluid sample absorbed by the reactant pad. The systems may involve absorbent pads separated by a substantially non-wettable mesh or a film which serves to wipe away excess sample from the reactant pad. There is no indication that the assay will not be started until sufficient sample is applied to the pad; rather, this device is concerned with excess sample applied to the device.

Allen et al., in U.S. Pat. No. 4,999,287, disclose a stripstick for analysis which includes means for automatically metering the volume of a sample so as to prevent excess of sample from interfering with the assay. Where the sample pad is to serve as the sample volume measuring device, the pad will have one side exposed for receiving the sample and the other side in contact with a porous, non-wettable film which is in contact with an absorbent layer. The sample will saturate the sample pad, and any residual fluid will overflow through the porous film and be absorbed by the absorbent layer so that a fixed amount of sample fluid is taken up by the pad. There is no provision for ensuring that a minimum amount of sample is applied to the pad.

Grenner, in U.S. Pat. No. 4,906,439, discloses a biological diagnostic device comprising a diagnostic test element and a sample application unit comprising a fluid delivery element comprising a layer having a plurality of grooves or channels in the surface thereof which is adjacent to the test element. The grooves can be made very small so as to deliver a small volume of precisely metered sample fluid to the device.

Engelmann, in U.S. Pat. No. 4,738,823, discloses a test strip with a preselected sample absorption capacity. Absorbent material is provided to remove excess sample applied to the reagent strip. However, there is no provision for ensuring that enough sample has been applied to conduct a test.

Burkhardt et al., in U.S. Pat. No. 4,810,470, disclose a diagnostic device comprising a first bibulous matrix that is adjacent to and in contact with a second bibulous matrix. The second bibulous matrix has been treated with a reagent suitable for detecting a specific analyte. In addition, the reagent-treated second bibulous matrix and a portion of the untreated first matrix are covered with a liquid-impermeable coating or film which serves to assist in metering the liquid sample into the first and second bibulous matrices and to act as a barrier to prohibit the test sample from directly contacting the reagent-treated bibulous matrix. The reagent-treated assay area of the matrices absorbs liquid test sample only up to the point of matrix saturation. This device prohibits excess sample from entering the assay area of the device, but does not ensure that sufficient sample enters the assay area of the device.

Lange et al., in U.S. Pat. No. 4,605,629, disclose a method for improving elution of reagent from a reagent strip. The reagent strip is provided with a handle, on the lower part of which is affixed an absorbent carrier impregnated with a reagent. The absorbent carrier is pressed against the handle by a thin, carrier-covering mesh which is stuck or sealed on to the handle on opposite sides of the carrier.

Zuk et al., in U.S. Pat. No. 4,435,504, disclose an immunochromatographic assay with a support having bound "mip" or antibody and a second enzyme. This assay measures the amount of analyte in a sample solution of a body fluid by combining a premeasured volume of sample with a premeasured volume of a solution of enzyme labelled analyte and immunochromatographing the solution or employing a combination of enzymes wherein one enzyme is the label and the other enzyme is affixed to the chromatographic support. The assay of this invention is performed by contacting the immunochromatograph with the sample containing solution. The sample traverses a region of the immunochromatograph by elution or solvent transport. The device used in this assay has a region in which the antibody is non-diffusively bound to a bibulous support. The analyte from the sample and its enzyme labelled conjugate traverse this zone along with the solvent. The analyte and its enzyme labelled analogue become bound to the support through the formation of an antibody complex. The signal producing system provides the area in this region with a color change which identifies the distance from a predetermined point over which the analyte and its enzyme labelled conjugate have travelled. In this manner, a quantitative determination of the analyte can be made. This assay does not directly test whole blood, and requires accurate volumetric measurement of the sample and the enzyme conjugate solution and dilution of the sample by a separately applied solvent. Furthermore, using this method to determine analyte concentration requires the use of a separate signal producing system. There is no immediate determination of the concentration of an analyte.

Zuk, in U.S. Pat. No. 4,594,327, discloses an assay method for whole blood samples. This assay requires at least one specific binding pair which is substantially uniformly bound to a solid bibulous element. The method of this invention requires that the sample be mixed in an aqueous medium with a binding agent, as well as a separate signal producing system such as discussed above. There is no provision of a self-contained unit that accurately determines the concentration of an analyte without the use of additional solvents or reagents.

Sloan et al., in *Clin. Chem.* 30:(10) 1705–1707 (1984), disclose a test strip which provides a quantitative measurement of chloride and sodium concentrations in urine. The test strips rely on wicking alone, and do not provide an additional capillary channel to speed up movement of the sample. The porous matrix typically requires between 15 and 30 minutes to draw urine up the entire measurement zone. This device does not provide a rapid quantitative test, a channel or a separation means for solids.

Hochstrasser, in U.S. Pat. Nos. 3,964,871 and 4,042,329, discloses a method and device for detecting either glucose or cholesterol. The device is dipped into a sample of body fluid, and the fluid reacts with an analyte. The concentration of the analyte correlates with a color intensity scale which translates into an approximate quantitative determination of the analyte. These tests, however, do not analyze whole blood.

Blatt et al., U.S. Pat. No. 4,761,381, disclose a volume metering capillary gap device for applying a liquid sample onto a reactive surface. The device controls a liquid volume flowing onto a reactive surface by means of an overflow chamber. The capillary channel leading to the overflow chamber is controlled so that liquid cannot flow back into a reaction chamber. The analytical method introduces liquid very quickly into the device (within 2 seconds) in order to prevent slow entry by simultaneous capillary action in the channel and wicking through the porous matrix at the bottom of the device. The geometry of the detection chamber determines the volume used for the test. Two compartments are connected in parallel to the sample entry port, i.e., liquid flowing from the entry port into the overflow chamber does not flow through the reaction chamber.

The geometry of the reaction chamber, through rectangular, is not channelled, nor is it suitable for a measurement scale. Although this device can receive blood as a sample fluid, there is no means for separating cells from plasma.

Ramel et al., U.S. Pat. No. 4,959,324, disclose a self-contained assay device using two strips separated by a gap wherein a flow path is completed by movement of a sample receiving pad into the gap. The movement of the sample receiving pad also results in release of a reagent solution which is then transported through the pad into a quantitation area, where the amount of analyte may be determined.

Hillman et al., U.S. Pat. No. 4,756,884, disclose a capillary flow device which provides for measuring a sample, mixing the sample with reagents, defining a flow path and reading the result. The capillary tube of this device provides the sole driving source for the movement of liquid through the device. The use of this device primarily involves tests requiring blood agglutination and optical readers to determine test results. There is no self-contained quantitative analysis means for measuring analytes.

Vogel et al., U.S. Pat. No. 4,477,575, disclose a process and composition for separating plasma and serum from whole blood. The device uses glass fibers having an average diameter of from $0.2\ \mu$ to $0.5\ \mu$ and a density of $0.1\ g/cm^2$ to $0.5\ g/cm^2$. The total volume of the plasma or serum separated from the blood is limited to at most 50% of the absorption volume of the glass fiber layer. Other fibers may be useful in forming the matrix with the glass fibers. There is no provision for metering plasma flow through the device nor a quantitative analysis of an analyte.

Ramel et al., U.S. Pat. No. 4,959,324, disclose an assay device for detecting or quantifying an analyte by measuring the distance of a detectable signal from a predetermined site. The device uses two strips separated by a gap, where a flow path is completed by movement of a sample receiving pad into the gap. The movement of the sample receiving pad also results in release of a reagent solution which is then transported through the pad into the quantitation area where the amount of analyte may be determined.

SUMMARY OF THE INVENTION

It is an object of the present invention to overcome the aforementioned deficiencies in the prior art, and, in particular, to provide means for measuring a fluid sample prior to initiating an assay to ensure that the amount of fluid sample applied is sufficient to conduct the desired test. Such means may be incorporated into a self-contained chromatic quantitative analyzer for quantitatively detecting an analyte in a biological fluid, such as whole blood.

Desirably, this analytical device can be used by a lay person and does not require pre-measurement of the sample. It is contemplated that one may provide an analytical device which measures the sample introduced therein and which does not initiate the analytical process unless there is sufficient sample to complete the analysis.

In another aspect, the present invention relates to providing a means for controlling flow of fluid through a detection zone so that the resulting colored column is not "rocket shaped".

According to one embodiment of the present invention, a sample well means is provided on a measuring device. This sample well means includes a well for receiving a sample, and means from which the sample is transferred to the remaining parts of the measuring device. The well is designed such that the analytical process will not be triggered until a certain minimum amount of sample has been deposited in the well. This minimum amount of sample must be sufficient to fill the entire metering or measuring areas of the device, thus avoiding interruption of the analytical process on one side, and insuring that there are no inaccurate results which might result from insufficient amounts of sample deposited on the device.

The sample well means is located on the test device such that the sample well means is positioned at a lower level than the first location to which the sample must be applied, hereinafter referred to as the initiation area. The sample well means is connected to the initiation area by a siphon means which is created by a channel between one of the ascending surfaces of the sample well and a flat tab protruding into the well. Surprisingly, this configuration functions as a siphon although the sides of the tab are not attached directly to the well. The minimum amount of sample required for conducting an assay on the particular assay device is determined, and the sample well means is constructed so that this amount of sample will trigger the assay. Thus, when the liquid sample is of a sufficient volume to conduct an accurate measurement, the fluid sample flows from the sample well means into the siphon means and into the initiation area of the measurement device. Sample thus is not drawn from the sample well unless there is sufficient sample to conduct a measurement.

The initiation area of the measurement device may be any area on the measurement device that can be used to hold a sample prior to testing. The initiation area may consist of an absorbent material such as fiber glass paper or loosely woven fabric, a capillary network, or some other construction such that, when the sample contacts the initiation area, the sample is drawn to this area.

The present invention is thus designed to ensure that only a sample above a minimum volume is drawn into a test device.

In one embodiment of the present invention, a fluid sample measuring device comprises three distinct parts:

1. a sample well into which sample is introduced so as to meter the sample to ensure that sufficient sample is present to conduct an assay;

2. an assay initiation area located at a level above the sample well; and 3. siphon means for connecting the sample well and the assay initiation area by which liquid can readily flow, resulting in a siphoning action from the sample well to the assay initiation area.

To ensure that sufficient sample is applied to the test device to provide an accurate reading, the sample well is located in front of the assay initiation area, and the sample well and the assay initiation area are connected by a siphon means so that sample can be drawn through the siphon means from the sample well into the assay initiation area.

The assay initiation area can be of any construction which can contain a fluid sample, such as a porous pad or an open well, or any matrix. In one embodiment of the present invention, the sample well comprises an open well into which the user drops a few drops of fluid sample, such as blood from a finger stick.

The siphon means is preferably constructed such that it exhibits little or no capillary activity, so that the level of liquid in the siphon means is approximately the same as in the sample well. The siphon means is conveniently created by a channel between one ascending surface of the sample well and a flat tab protruding into the bed.

The initiation area is connected to a detection zone where the assay occurs. This detection zone includes an indicator means, such as a chromatographic indicator system, to display quantitatively the amount of analyte in the sample. At least one indicator means is immobilized in the detection zone in a calibrated or predetermined concentration. In the detection zone, the fluid sample interacts with the indicator means. The indicator means detects the analyte in the fluid sample by reacting with the analyte, a reaction product of the analyte, or a labelled analogue, developing a color detectable signal, such as a color. The detectable portion of the detection zone caused by reaction of the indicator means with the analyte, or a derivative thereof, as observed after the capillary action is terminated, corresponds to the concentration of the analyte in the fluid sample. A scale is provided along the length of the detection zone channel to readily equate the detectable portion of the channel to the concentration of analyte.

To quantify an analyte using a device of this invention, a fluid sample is deposited into the sample well means. If there is sufficient volume of sample to conduct an assay, the sample is drawn up into the assay initiation area through the siphon means. There may be a separation zone below the assay initiation area to remove any solids suspended in the fluid sample. The fluid sample is then drawn through the detection zone by capillary and/or wicking action, preferably to a reservoir means, which contains an absorbent. The reservoir means draws the fluid sample through the detection zone and, when the reservoir is filled with the fluid sample, the capillary and/or wicking action is terminated. While the fluid sample is being drawn through the detection zone, the indicator means is permeated with the fluid sample. The detection zone includes a suitable indicator immobilized therein in a predetermined concentration to react with the analyte. Thus, the analyte in the fluid sample is completely reacted in a single step or a series of chemical reactions with the indicator means.

In another embodiment of the present invention, the assay initiation area comprises an absorbent pad, with a plastic tab extending into the sample well to create a siphon tube.

In order to prevent the development of a rocket-shaped curve to the colored detection column, the flow of the liquid through the detection zone can be forced through a tortuous path. This tortuous path can be effected by providing a roughened or knurled surface at the bottom of the detection zone, or by introducing a mesh-like fabric into the detection zone to break up the flow of the fluid through the detection zone.

The indicator means can be immobilized in the detection zone in a variety of ways. For example, a membrane can be provided onto which the indicator means is immobilized, or the indicator can coat the fibers of the mesh used to break up the path of the fluid flowing through the detection zone. Thus, the flow through the detection zone as well as the path to and through the indicator means can be controlled by varying the configuration and materials of the detector.

DETAILED DESCRIPTION OF THE INVENTION

Figure 1:
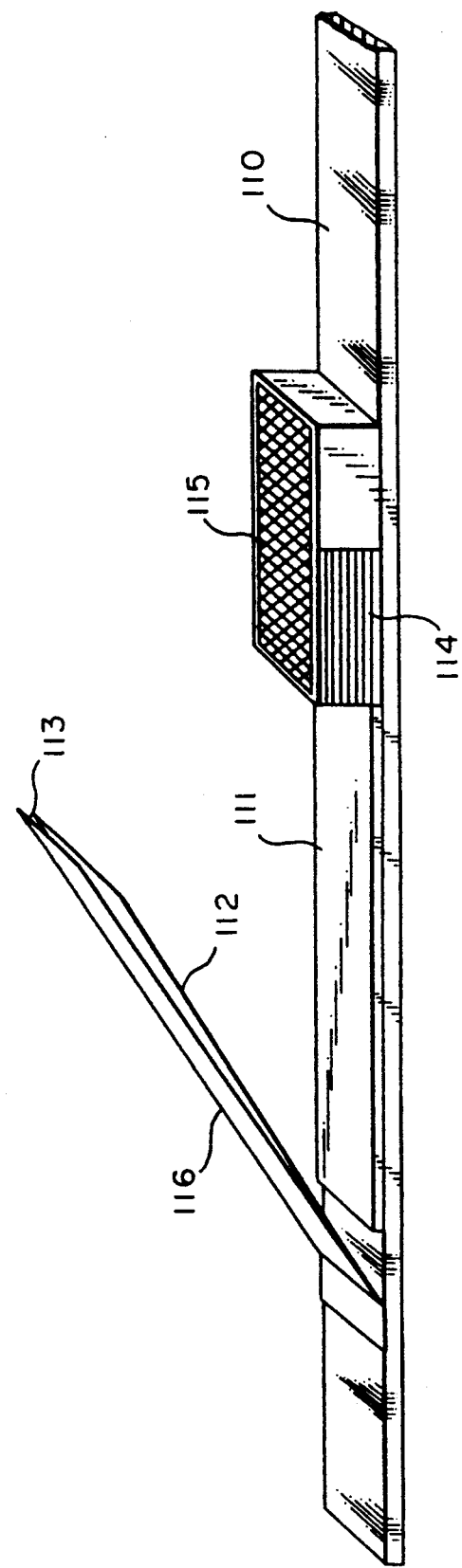
FIG. 1 shows a cross-section of one type of conventional analyzer system.

An example of a previously used assay device is the disposable reagent Reflotron TM whole blood analyzer produced and marketed by the Boehringer Mannheim Corporation in Indianapolis, IN, shown in FIG. 1. The disposable device is described more completely in U.S. Pat. No. 4,477,575, which is hereby incorporated in its entirety by reference. This device uses whole blood without pretreatment, and generates results within less than three minutes. In use, blood is deposited onto small strips consisting of several zones made made of bibulous material in which chemicals are embedded.

In the commercial device shown in FIG. 1 a support 110 is provided upon which rests a plasma reservoir 111. Reagent layer 112 overlies and will usually be pressed into the plasma reservoir, and indicator layer 113 is located above the reagent layer. A plasma separation layer is provided at 114, which is covered by a protective layer 115. A transparent protective layer 116 overlies the indicator layer 113. Plasma penetrates this area quickly after a metered sample of whole blood is added to the protective layer 115. After inserting the device into the Reflotron TM instrument the reaction layer and indicator layer are both pressed mechanically into the plasma reservoir 111.

Figure 2:
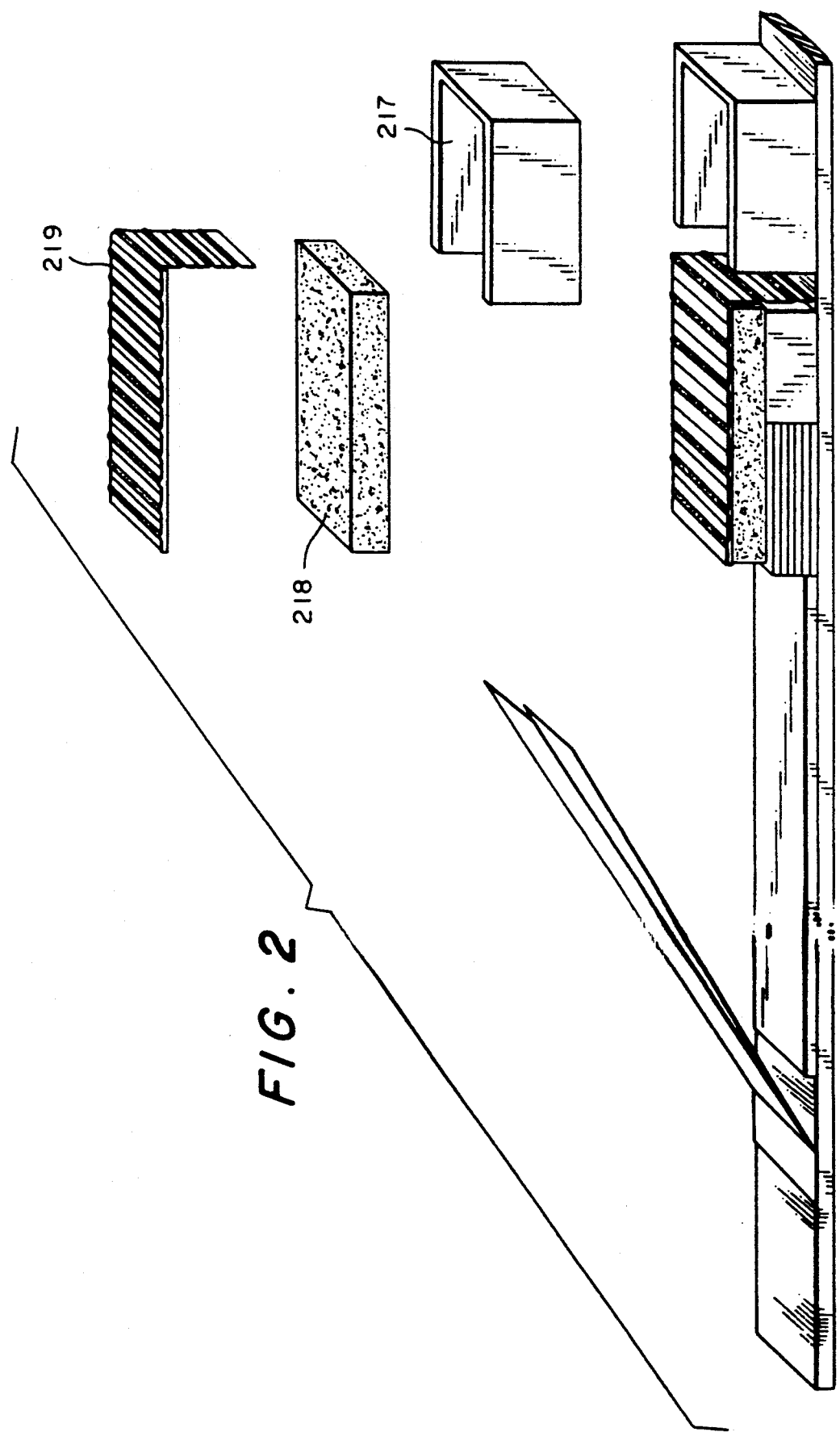
FIG. 2 shows an exploded oblique view of a device according to the present invention which can be produced by retrofitting a conventional analyzer system.

FIG. 2 shows the device described in FIG. 1 without the protective layer 115. Instead, three elements, a sample reservoir 217, an absorbent pad 218 and a new protective layer with a siphon tab 219, have been added to the device. These additional elements allow the user to add whole blood to the device without metering it beforehand.

The amount of sample added to this initial reservoir can vary from about 20 to about 100 $\mu$liters. The upper and lower limits of volume capacity for this first reservoir are only limited by the physical manufacture of the reservoir, not by the functioning of the device. For example, the first reservoir could be designed to contain as little as 10 $\mu$liter or as much as 1.0 milliliter of sample, depending upon the manufacture and purpose for use of the device.

Figure 3:
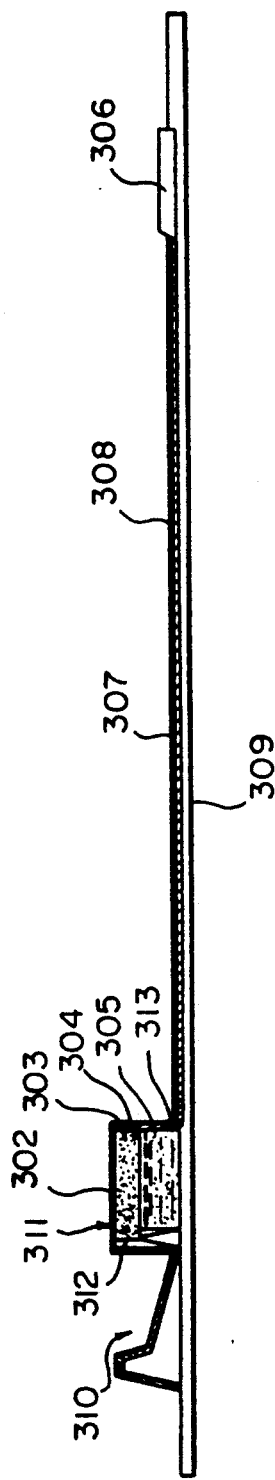
FIG. 3 shows a cross section of another embodiment of a device according to the present invention.

As shown in FIG. 3, the sample well 310 is separated from the assay initiation area 311 by locating the assay initiation area at a level higher than the sample well reservoir. The sample well and the assay initiation area are connected by means of a siphon means 312 consisting of a plastic tab extending from the top of the assay initiation area 311 through which fluid can be conveyed from the sample well to the assay initiation area. An outlet 313 from the assay initiation area is provided so that the sample may exit from the assay initiation area into a channel 308.

As shown in FIG. 3, the assay initiation area has a means 304 for separating solids from the fluid sample, so that the device can be used for testing fluids that either have or do not have suspended solid matter. The presence of a means for separating or partially withholding solids ensures that only a liquid being tested is exposed to the channel of the device. In this manner, cells and other suspended solids are prevented from proceeding further by fiberglass paper, porous plastic, glass beads or semi-permeable membranes. Many varieties of these materials are commercially available.

The measuring device is supported on a plastic support 309, and a transparent cover 302 overlies the assay initiation area.

The measurement channel 308 contains or encloses at least one reagent for detecting the presence of a selected of compounds and/or enzymes that react simultaneously or sequentially with the selected analyte to produce a detectable reaction product. Desirably, the detectable reaction product produces a color change that is visible to the naked eye.

A great variety of reagents for detecting the presence of an analyte in a fluid sample are known in the art and are commercially available. These reagents must be immobilized in some fashion either on the wall of the channel or in a material that is, desirably, stationary within the channel. When more than one reagent is required to detect an analyte, the reagents are, desirably, immobilized in their reaction sequence within the channel or within the first open reservoir and the channel.

The reagent that produces the detectable or chromatic reaction product must be present in a calibrated or predetermined concentration within the channel. The term "chromatic chemical indicator" is used in this sense to include the reagent or combination of reagents necessary to detect a selected analyte in a fluid sample, including a chromatic chemical indicator to produce visible results. The term "predetermined concentration" is used herein to include a concentration of one or more chromatic chemical indicators and/or other reagents that is necessary, in accordance with the present invention, to produce the reaction results desired for a particular test.

The preferred embodiment of the present invention has a material that is stationary within the channel and provides dye layer in the chromatic reaction zone 307. This material is preferably a natural or synthetic membrane. Suitable membranes for use in this invention are capable of receiving and immobilizing the selected chromatic chemical indicator and are chemically compatible with the selected chromatic chemical indicator. Suitable membranes are commercially available and can be porous or fibrous materials including filter paper or nylon cloth. The membrane is desirably an integral part of the channel, such as the bottom of the channel, and is sealed in place.

A preferred embodiment of the invention has at least two zones on the membrane within the channel. An initial reaction zone 305 provides reagents to mix and react with an analyte without formation of color to form an intermediate compound. A chromatic reaction zone with dye layer 307 provides reagents to mix and react with the intermediate compound to cause color formation. Many combinations of multiple zone reactions, with or without the formation of intermediate compounds, can be provided with the present invention.

The device includes means for metering the volume of fluid sample that passes through the channel. This means for metering is, desirably, a "pull" compartment 306 or a reservoir filled with an absorbent also called the draw zone. The geometry, physical nature, and method of incorporation of this pull compartment and the channel can be configured to meter precisely the volume and rate of flow of the biological material through the channel. The pull compartment, also called the draw zone, can contain absorbent or porous materials such as filter paper or porous plastic materials to control further the volume and/or rate of flow of the biological material through the channel. Alternately, the measurement channel can have a knurled surface so as to control the shape of the fluid flow therethrough.

The means for metering the volume of fluid sample in the channel can include a variety of geometric configurations and/or combinations of materials. The void volume of the reservoir is the most critical parameter of the means for metering the flow of sample. The density and composition of the material or membrane in the channel as well as the density and composition of any material which is optionally present in the reservoir can be another parameter for altering the flow of the sample. For example, the hydrophilic character of materials in the channel or of a thermoformed moisture barrier used to manufacture the lower surface of the channel significantly affects the flow of a fluid sample through the device. The reservoir, in the preferred embodiment of the invention, contains an absorbent of precise volume and precise solid volume. The reservoir draws a precisely metered amount of liquid through the channel. The reservoir or draw zone thus provides a self-metering feature for the device.

Regardless of the materials or geometric configuration chosen, it is desirable that effective and complete interaction of the analyte in the fluid sample or a derivative thereof occur with the chromatic chemical indicator. The means for metering the flow of a fluid sample in this invention preferably provides a quantitative assay result in at least ten minutes, and, more preferably, in at least three minutes.

The dimensions of the device according to the present invention can vary with the intended use. Factors that can vary the dimensions of the device include the amount or nature of the chromatic chemical indicator necessary to perform the desired test for a concentration of analyte in a fluid sample to be tested. The dimensions of the device can be selected to control the reaction time of analyte and chromatic chemical indicator and to control the time required to complete the test. Generally, the device is about 70 to 200 millimeters long, about 20 to about 30 millimeters wide, and about 3 to about 15 millimeters high. The opening, through which the sample is placed into the sample well, is desirably between about 3 millimeters and about 15 millimeters. The initiation area is preferably between about 6 millimeters and 35 millimeters in total length, including the opening to the initiation area, and between about 8 millimeters and about 15 millimeters in width. The channel is desirably a length sufficient to permit the analyte and chromatic chemical indicator to interact and perform the desired analytical test. The dimensions are desirably sufficient to permit capillary action of the fluid sample. A channel that permits capillary action to occur is desirably between about 50 millimeters and 150 millimeters in length and between about 2 millimeter and 6 millimeters in width. The reservoir may be between about 10 millimeters and about 30 millimeters in length and about the same width as the initiation area.

To use the device according to the present invention, a fluid sample is transferred to the sample well 310, shown in FIG. 3. If the sample has a volume of less than 40 μliters, 40 μliters being the amount required by this embodiment of the device to complete the analytical reaction, the sample will not be drawn into the assay initiation area 311 of the device and the test would not begin. If a sample of less than 40 μliters is added to the sample well, for example, 35 μliters, the top surface of the sample would be below the level of the absorbent pad 303 in the initiation area. It is important to the proper functioning of this device that the siphon means 312 exhibit little or no capillary pull of its own so as not to draw the sample up to the level of the reservoir. It is also desirable that the initiation area not be airtight when the liquid enters the siphon tube, which would cause a buildup of pressure in the absorbent rad. This buildup of pressure could prevent the sample from being drawn out of the initiation area. Given these two conditions, sample would not be drawn into the device if 35 μliters of sample were added to the sample well, since the liquid level in the siphon tube would not be high enough to contact the initiation area. However, if 40 μliters of blood were added to the sample well, the sample level in the siphon means would be high enough for the blood to contact the absorbent material or capillary network of the initiation area. This allows the sample to be drawn from the sample well into the initiation area until the initiation area is full. The void volume of the initiation area is preferably chosen such that sufficient sample would be drawn from the sample well in order to complete the test. For example, if the test required 40 μliters to go to completion, and exactly 40 μliters were transferred to the sample well, all of the sample would be siphoned from the sample well into the initiation area. If 100 μliters of sample were added to the sample well, 40 μliters would immediately be siphoned into the initiation area, and 60 μliters would remain in the siphon tube and the sample well without adversely affecting the test.

The initiation area can comprise an absorbent material such as glass fiber paper or loosely woven fabric, a capillary network, or some other construction such that when the sample contacts the reservoir material, it is physically drawn into the reservoir.

The material which forms part of the initiation area can be treated with chemicals which are to be intimately mixed with the sample. For example, when whole blood from a finger stick is used as the sample, an anticoagulant such as EDTA or heparin must be mixed with the sample to prevent the blood from clotting. If the absorbent material comprising the initiation area is pre-treated with an anti-coagulant, the blood and anti-coagulant are thoroughly mixed while the sample is drawn into the initiation area. This mixing is effected both by the large amount of treated surface exposed to the blood and also by the turbulent mixing which would occur as the sample is rapidly drawn into the device and the anti-coagulant is dissolved.

Figure 4:
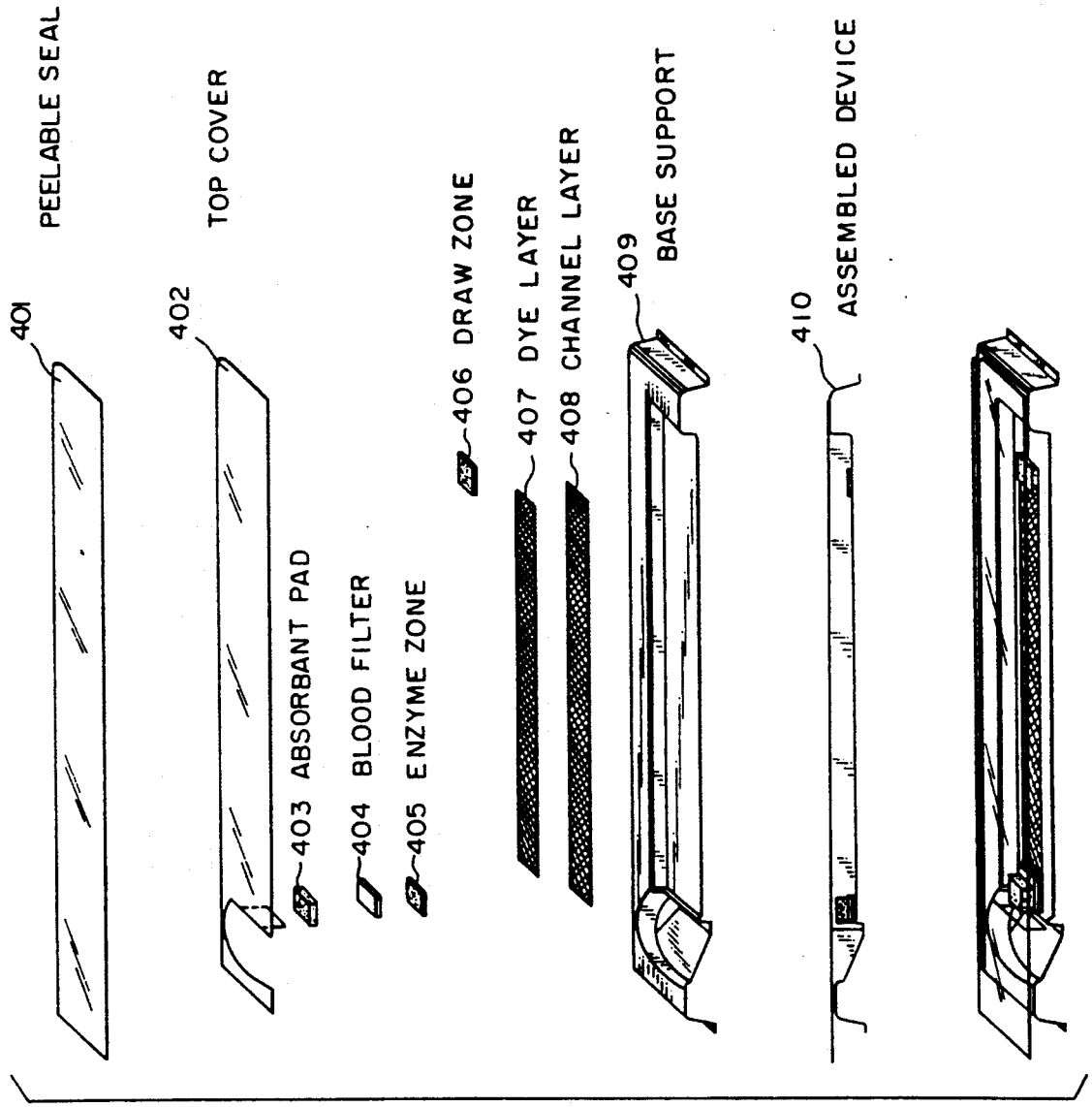
FIG. 4 shows an exploded cross section of the device of FIG. 3.

FIG. 4 shows an exploded view of the assembled device 410 in which each of the components of one embodiment of the device is shown individually. The device rests upon a base support 409, on which is placed a channel layer 408 which contains a dye layer or other indicator layer. The draw zone 406 aids in moving the fluid sample from the initiation area through the measurement channel 408. The sample is introduced to the device through an absorbent pad 403, which forms the assay initiation area. A blood filter 404 may be provided to filter unwanted solids from a sample of whole blood. The sample then contacts an enzyme zone 405 to begin the indication part of the assay. A top cover 402 covered with a peelable seal 401 protects the device from contamination during storage.

In a preferred embodiment of the present invention, the sample well is coated with or made of a hydrophilic material, such as polyvinylpyrrolidone. The use of a hydrophobic material for a siphon tube means may affect the level of sample inside of the siphon tube means, so that it is preferred to use a hydrophilic material for the siphon tube means, or the interior of the siphon tube means, as well.

In another embodiment of the present invention, the device uses a linear measurement zone which is longer than two cm and shorter than about 20 cm. Within this linear measurement zone, hydrogen peroxide, formed when the sample containing, e.g., cholesterol, contacts a suitable enzymatic reagent prior to entering the linear measure zone, is continually depleted from the front of the fluid sample in the channel by a peroxidase-dye reaction. The fluid sample exits the measurement zone and is drawn into an absorbent pad in the reservoir, also referred to as the draw zone, which precisely meters the amount of fluid which flows through the channel. Ideally, the fluid flow in the channel is first in, first out. It is preferable that hydrogen peroxide be depleted from the fluid sample, and that the hydrogen peroxide depleted fluid then always remains downstream of fluid sample which has not yet depleted of hydrogen peroxide. A laminar flow effect, wherein liquid next to the surface boundaries of the channel flows more slowly than liquid in the center of the channel, is undesirable. A laminar flow effect continuously supplies the front of the liquid column with new fluid which has not been depleted of hydrogen peroxide. Even a partial laminar flow effect could extend the front of dye color development and produce a rocket shaped color front instead of a sharp demarcation between reacted and unreacted dye.

To circumvent the time limitations imposed by wicking alone, the measurement zone preferably includes a channel about 10 cm long, about 0.2 cm wide, and about 0.0025 cm deep. Therefore, the fluid volume required to fill such a channel would be about 0.005 cubic centimeters, or about 5 μliters. An unmodified channel, however, would create certain problems. As the sample flows down the channel, it is in effect a thin film moving between two parallel surfaces, wherein the top and bottom surfaces provide most of the drag force resistance to the flow of the liquid. In addition, the sides of the channel, even though only about 1.25% of the length (in cross section) of the top and bottom surfaces, provide additional drag at the boundary layer. Since the fluid at the center of the liquid column always flows more rapidly than the fluid at the sides of the liquid column, the fluid front is continually being replenished with fluid further back in the liquid column, because the fluid at the sides of the column is flowing more slowly. This leads to the formation of a rocket shape at the dye front because fluid with unreacted hydrogen peroxide is flowing faster in the center of the channel than at the sides of the channel. This effect also occurs at the top and bottom surfaces of the channel, but would not be visible as a rocket shape (would not contribute to the rocket shape) because the dye is bound to either or both of the surfaces and would react at the point of contact with fluid containing hydrogen peroxide. Laminar flow effects could contribute to a fuzzy, undefined dye front or linearity problems.

Figure 5:
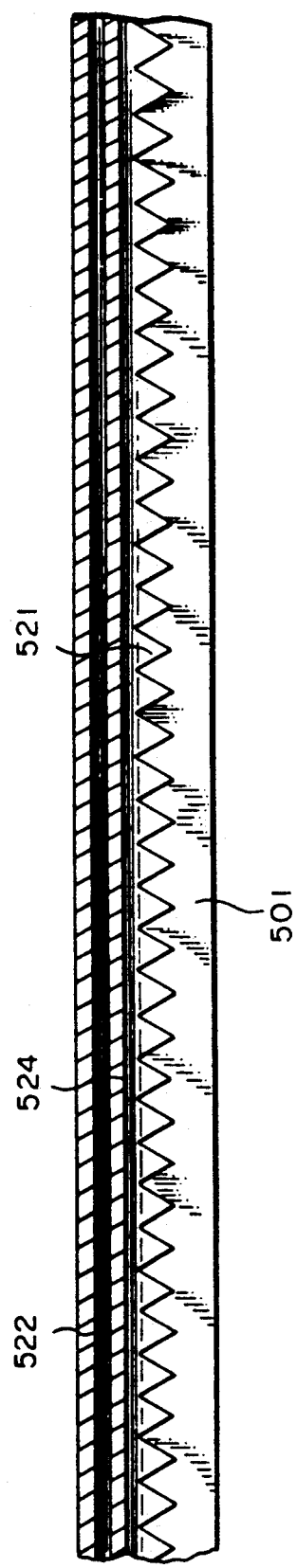
FIG. 5 shows mesh in the channel of the device according to the present invention.

One solution to the laminar flow problem is to create turbulence in the flow of fluid through the channel. This turbulence can be effected by any suitable means, such as by introducing a series of small ridges or protrusions on the bottom and/or top surface of the channel, hereinafter called a knurled surface (FIG. 5). This knurled surface introduces turbulent flow into the liquid column moving through the measurement zone of the device. This turbulent flow causes random mixing within any given cross-section of the channel, but not along the length of the channel.

Figure 6:
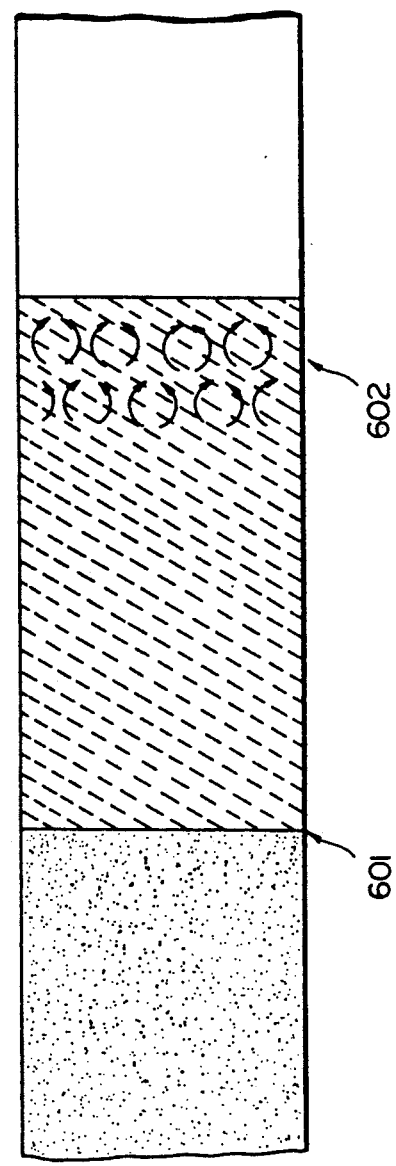
FIG. 6 shows the fluid flow in a section of the measurement zone channel.

An example of such a knurled surface is a series of grooves cut at a 45 degree angle to the long axis of the channel (521), imprinted on the surface of the channel, and another series of grooves at a 90 degree angle to the first, to produce minute raised pyramids at the bottom of the channel (501). If these pyramids are 0.0025 cm high, the apex would touch the top surface of the channel (524). This converts the formerly open channel into a tortuous but well defined network of interconnecting fluid flow paths. As fluid flows through this channel network, it becomes impossible for liquid at the center to flow faster than liquid at the side because the flow at any given point in the channel is being constantly redirected. Therefore, a rocket shaped dye front will not occur. In addition, the definition of the dye front between colored (reacted) and uncolored (hydrogen peroxide depleted fluid and unreacted dye) (601) would be sharper due to the mixing caused by turbulent flow (602), as shown in FIG. 6.

Alternatively, turbulence can be introduced to the fluid flow by providing barriers to the fluid flow within the channel, which barriers are not necessarily a part of the channel. This can be done by including a mesh fabric in the channel. When the fluid contacts the fibers of the mesh, turbulence is introduced to the flow of the fluid, and the flow through the channel is constantly redirected, so that the dye front 80 appears flat.

In order to reduce the time required for the fluid sample to contact the indicator materials, the fiber of the mesh fabric can be coated with the indicator reagent materials.

The device and method of the present invention can be used for a number of different assays. These assays can include assays wherein the analyte of interest is converted to a reactive compound that is able to produce or destroy a dye. Additionally, these assays can include assays wherein the analyte of interest competes with a labelled derivative of itself for a limited number of binding sites supplied by a specific binder embedded in the membrane in the channel. The specific binder can be an antibody, an antigen, or a receptor molecule. After binding occurs, the labelled derivative is visualized in the detection zone of the channel by a reaction specific to the label. This can be an enzymatic reaction leading to a visible color change or the label itself can be visible in the device. Labels can include particles, liposomes loaded with dyes, and dyes per se.

The device and method of the present invention can be used for a large number of specific assays. The assays can involve the two general categories of assays discussed above which are chemical reaction assays and reactions involving binder assays. Examples of chemical reaction assays include tests for cholesterol, high density lipoproteins, triglycerides, glucose, uric acid and potassium. Examples of binder reactions, which involve antibodies, antigen or receptors, include (1) tests for viruses such HIV, rubella, and herpes, (2) tests for hormones to determine pregnancy and thyroid status, and (3) tests for drugs such as digoxin, phenobarbital, and theophylline, as well as many others.

The membranes used in the device of the present invention may be "activated" membranes. Activated membranes have reactive chemical groups which react with amino and carboxyl groups of proteins, antibodies and dyes in order to form covalent bonds. Commercial sources for suitable membrane materials include those sold by Millipore Intertech, Bedford Ma. These membranes are designated Immobilon-AV Affinity Membranes. These membranes consist of chemically derivatized hydrophilic polyvinylidene fluoride. Alternative membranes are those supplied by Pall Biosupport Corporation, Glen Cove, N.Y. These membranes are called Immunodyne membranes, and consist of chemically modified Nylon 66. Gelman Sciences, Inc. of Ann Arbor, Mich., provides Ultrabind Membranes, the chemical composition of which is not available.

The device may include a top cover consisting of clear 0.015 inch thick PVC roll stock. The bottom base is the same material and can also be manufactured from PVC or a polyethylene laminate containing a moisture barrier such as SARAN. A removable peel-off protective strip, covering the upper surface of the device may be provided. This strip consists of polyethylene-laminated aluminum foil which also serves as a moisture barrier.

The following examples are for illustrative purposes only, and are not meant as limitations of the invention.

CHOLESTEROL ASSAY

Procedures

Whole blood, obtained from a finger prick, is transferred into the sample well 310 of FIG. 3. If there is sufficient blood to conduct an assay, the blood in the well travels to the assay initiation area 311 of the device. The means for separating solids 304 retains the bulk of the red cells. Cell free or cell poor plasma enters the initial reaction zone 305, also called the enzyme zone, which contains the enzymes cholesterol esterase and cholesterol oxidase and certain salts and solubilizers such as surfactants. The initial reaction zone also contains the enzyme horseradish peroxidase. Plasma cholesterol is converted to cholestenanone and hydrogen peroxide in the initial reaction zone.

The plasma containing these reaction products and the other reagents dissolved in the initial reaction zone enter the channel 308, which contains a precise amount of a dye immobilized in a physical matrix which is a membrane. In the presence of horseradish peroxidase, the dye is quantitatively oxidized by hydrogen peroxide and converted into a colored species. The dye is evenly distributed in the compartment, and its conversion occurs immediately upon contact with hydrogen peroxide. Therefore, the length of the color converted area is proportional to the amount of hydrogen peroxide, and, therefore, to the amount of cholesterol in the sample.

Plasma, devoid of hydrogen peroxide, enters the draw zone chamber. While the draw zone is being filled, the oxidation of the dye in the channel continues until the draw zone is completely filled, at which time the process stops. The length o the color bar formed in the channel is read from a scale which has been calibrated in cholesterol concentration units.

Theophylline Assay

The materials and procedure are the same as those described above except as follows:

PROCEDURE

Whole blood first enters the sample well, from which it enters the assay initiation area as previously described. Blood cells are retained in this compartment and plasma moves via wicking action into the initial reaction zone. The initial reaction zone contains a conjugate of theophylline and horseradish peroxidase in predetermined, precise quantities. When cell-free or cell-poor plasma enters the channel, a precise volume of plasma completely takes up the theophylline conjugate and a homogeneous solution of the theophylline conjugate in plasma is generated. The drug derivative is distributed in the initial reaction zone in the form of a thin film covering the exterior and interior surfaces of the porous material which constitutes the zone. The initiation reaction zone is designed such that plasma is capable of entering it very rapidly without immediately entering the channel of the measurement zone. The first open reservoir and the initial reaction zone also contain chemical additives which release plasma protein bound theophylline.

The homogeneous mixture moves into the channel which contains a precise amount of antibody against theophylline. The antibody is evenly distributed over the compartment and immobilized on the compartment along with a dye that is oxidizable by peroxide in the presence of horseradish . peroxidase. A dry hydrogen peroxide such as urea peroxide is also embedded in the membrane of the channel. The antibody against theophylline also reacts with the theophylline horseradish peroxidase conjugate.

When theophylline is absent from the plasma, the theophylline conjugate is taken up by the antibody in the very first section of the channel. However, in the presence of theophylline, which competes with the conjugate for the limited number of antibody sites on the solid matrix in the channel, some of the antibody sites in the channel are being blocked by plasma theophylline. With increasing concentration of theophylline in the plasma, the last unbound conjugate molecule must travel farther and an increasing distance through the channel in order to find an immobilized binding partner. The fraction of the channel traversed to find an immobilized conjugate, therefore, becomes longer with increasing concentration of theophylline in the plasma.

The theophylline horseradish peroxidase conjugate color converts the immobilized dye in the channel through oxidation with peroxide along its migration path. This process stops after the last conjugate molecule becomes immobilized. This process results in a color bar whose length is proportional to the concentration of drug in the whole blood sample.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

TABLE OF ELEMENTS IN DRAWINGS 110 support
111 plasma reservoir
112 reagent layer
113 indicator layer
114 plasma separation layer
115 protective layer
212 support
216 plasma separation layer
217 sample well
218 absorbent pad
219 protective layer with siphon tab
220 measurement channel
230 enzyme layer
302 transparent cover
303 absorbent pad
304 solids separating means
305 initial reaction zone
306 pull compartment
307 chromatic reaction zone
308 measurement channel
309 support
310 sample well
311 assay initiation area
312 siphon means
313 outlet
401 peelable seal
402 top cover
403 absorbent pad
404 blood filter
405 enzyme zone
406 draw zone
407 dye layer
408 channel layer
409 base support
410 assembled device
501 raised pyramids
521 channel
524 top of channel
601 dye front
602 turbulent flow

What is claimed is:

1. A measuring device for detecting an analyte in a fluid sample comprising:
    a sample well means for measuring the amount of fluid sample applied to said measuring device;
    an assay initiation area located above the level of said fluid sample well;
    a siphon means connecting said sample well to said assay initiation area, whereby fluid sample will not contact and fill said assay initiation area unless a predetermined minimum amount of fluid sample is deposited in said fluid sample well, and a measurement channel in fluid communication with said assay initiation area, said measurement channel including a carrier on which is absorbed at least one indicator means for detecting the analyte of interest.

2. A device for detecting analyte in a fluid sample comprising:
    a measuring device according to claim 1 wherein said assay initiation area is connected to a reservoir means through measurement channel.

3. The device according to claim 1 wherein said carrier is a membrane.

4. The device according to claim 1 wherein said channel includes obstacles therein which cause frequent changes in the direction of flow of said fluid sample.

5. The device according to claim 4 wherein said obstacles are in the form of a knurled surface in said channel.

6. The device according to claim 4 wherein said obstacles are in the form of a mesh.

7. The device according to claim 6 wherein said mesh is impregnated with a chromatic chemical indicator.

8. The device according to claim 2 wherein said assay initiation area includes a filter means to filter solid particles from said fluid sample.

9. The device according to claim 2 wherein said assay initiation area comprises at least one absorbent pad.

10. The device according to claim 2 wherein said assay initiation area and said reservoir means each comprise at least one absorbent pad.

11. The device according to claim 1 wherein said sample well is constructed of or coated with a hydrophilic material.

12. The device according to claim 1 wherein said siphon means is constructed of or coated with a hydrophilic material.

13. In a strip assay device for quantifying the amount of analyte in a fluid sample, said device comprising a detection zone containing a reagent that reacts with analyte in the fluid sample to provide a visual indication of the presence of the analyte, the improvement comprising preventing initiation of an assay in the device if there is insufficient sample present to conduct a reliable assay, by providing on said device;
a fluid sample well means;
an assay initiation area located above the level of said fluid sample well; and
siphon means connecting said sample well to said assay initiation area, whereby fluid sample will not contact said assay initiation area unless a predetermined minimum amount of fluid sample is deposited in said fluid sample well.

14. A process for ensuring that sufficient fluid sample is present to conduct an assay comprising:
introducing said fluid sample into a sample well means located below an assay initiation area, and which sample well means is connected to said assay initiation area by a siphon means, whereby if sufficient sample is present to initiate an assay, the sample will flow up the siphon means from the sample well means to the assay initiation area; and noting if sample flows up the siphon means from the sample well.

15. A process for detecting an analyte in a fluid sample comprising:
introducing said fluid sample into a sample well means which is located below an assay initiation area, and which sample well means is connected to said assay initiation area by a siphon means, whereby if sufficient sample is present to initiate an assay, the sample will flow up the siphon means from the sample well means to the assay initiation area; and, if there is sufficient sample present to initiate an assay,
permitting the fluid sample to flow through the assay initiation area into a measurement channel;
permitting the fluid sample to flow through a measurement channel having a carrier on which is absorbed at least one indicator means for detecting the analyte of interest, said measurement channel being connected to a reservoir means whereby said reservoir means draws fluid sample through said measurement channel; and
detecting the amount of analyte by reading the indicator means.

16. The process according to claim 15 further including obstacles in said measurement channel whereby said fluid sample changes flow direction while flowing through said measurement channel.

17. The process according to claim 16 wherein said obstacles are in the form of a knurled surface in said measurement channel.

* * * * *